United States Patent [19]

Knifton et al.

[11] Patent Number: 5,716,896
[45] Date of Patent: Feb. 10, 1998

[54] ONE-STEP SYNTHESIS OF METHYL T-BUTYL ETHER FROM T-BUTANOL USING β-ZEOLITE CATALYSTS MODIFIED WITH LITHIUM PLUS RARE EARTHS

[76] Inventors: John Frederick Knifton, P. O. Box 15730, Austin, Tex. 78761; Pei-Shing Eugene Dai, P. O. Box 1608, Port Arthur, Tex. 77641

[21] Appl. No.: 346,449

[22] Filed: Nov. 29, 1994

Related U.S. Application Data

[62] Division of Ser. No. 181,143, Jan. 12, 1994, Pat. No. 5,387,723.

[51] Int. Cl.[6] ..................................................... B01J 31/00
[52] U.S. Cl. ..................................................... 502/113
[58] Field of Search ............................. 568/698; 502/113

[56] References Cited

FOREIGN PATENT DOCUMENTS 7432 of 1982 Japan.

*Primary Examiner*—Paul J. Killos
*Attorney, Agent, or Firm*—Kenneth R. Priem; James L. Bailey; Cynthia L. Hunter

[57] ABSTRACT

Disclosed is a method for producing alkyl tertiary alkyl ethers which comprises reacting t-butanol with an alkanol in the presence of a catalyst which exhibits extended life comprising β-zeolite modified with one or more metals selected from the group consisting of Group IA and Group IIIB of the Periodic Table and continuously contacting said alkanol and t-butanol in a molar amount from about 10:1 to 1:10 over said zeolite catalyst at a temperature of about 20° C. to about 250° C. and a pressure of about atmospheric to about 1000 psig.

13 Claims, 1 Drawing Sheet

ONE-STEP SYNTHESIS OF METHYL T-BUTYL ETHER FROM T-BUTANOL USING β-ZEOLITE CATALYSTS MODIFIED WITH LITHIUM PLUS RARE EARTHS

CROSS-REFERENCE

This is a division of application Ser. No. 08/181,143, filed Jan. 12, 1994 now U.S. Pat. No. 5,387,723.

This application is related to U.S. patent application Ser. Nos. 08/096,873, 08/057,373 abandoned and 08/148,248 abandoned.

It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917, 218 U.S. Pat. No. 5,214,217; 07/878,121 U.S. Pat. No. 5,214,218; and 07/917,885 U.S. Pat. No. 5,220,078, all of which are incorporated by reference herein in their entirety.

FIELD OF THE INVENTION

This invention concerns a process for preparing methyl tertiary-butyl ether (MTBE) along with isobutylene in one step by the reaction of tertiary butanol and methanol and the presence of a catalyst comprising β-zeolite modified with one or more metals selected from Group IA and IIIB of the Periodic Table, as defined in the Condensed Chemical Dictionary, 10 ed., p. 789. Preferred elements include lithium and the rare earth metals. The invention is especially advantageous in that the lithium, rare earth metal-modified β-zeolite gives conversion levels of ca. 70% for over 2000 hours of service, without loss of tBA conversion levels and with improved MTBE productivity in comparison with the prior art.

BACKGROUND OF THE INVENTION

Generally, it is known that asymmetrical $C_4$–$C_7$ alkyl tertiary alkyl ethers are particularly useful as octane improvers for liquid fuels, especially gasoline. Methyl tertiary butyl ether (MTBE), ethyl t-butyl ether (ETBE), isopropyl t-butyl ether (IPTBE) and tertiary amyl methyl ether (TAME) are known to exhibit high octane properties. Much attention has been focused on production of these ethers due to the rapidly increasing demand for lead-free octane boosters for gasoline.

It is known in the art to produce MTBE or ETBE by reacting isobutylene with either methanol or ethanol, resulting in the formation or MTBE of ETBE, respectively. The reaction normally is conducted in liquid phase with relatively mild conditions. The isobutylene can be obtained from various sources, such as naphtha cracking, catalytic cracking, etc. The resulting reaction product stream contains the desired MTBE or ETBE, as well as unreacted isobutene and other $C_4$ hydrocarbons and methanol or ethanol.

Since oxygenates are used as gasoline blending components, extenders, octane boosters and as key ingredients for reducing the emissions of CO and VOCs (Volatile Organic Compounds), it is expected that the demand for oxygenates will increase enormously in the coming years. See F. Cunill, et al., "Effect of Water Presence on Methyl tert-Butyl Ether and Ethyl tert-Butyl Ether Liquid-Phase Synthesis". Ind. Eng. Chem. Res. 1993, 32, 564–569.

Of all oxygenates, the tertiary ethers, such as methyl t-butyl ether (MTBE), ethyl tert-butyl ether (ETBE), and tert-amyl methyl ether (TAME) are preferred by refineries to lighter alcohols. They have lower blending Ried vapor pressure (BRvp), lower vaporization latent heats and low solubilities in water. The most common ether in use today is MTBE with a projected production of about 25 million metric tons.

With the expanding use of MTBE as an acceptable gasoline additive, a growing problem is the availability of raw materials. As mentioned, the critical raw material is historically isobutylene (Oil and Gas J., Jun. 8, 1987, p. 55). A number of recent patents to Texaco Chemical Co., noted below, use t-butanol, rather than isobutylene, in a one step reaction.

The main drawback of tertiary ethers, is that they substantially increase aldehyde emissions, which are under EPA regulations and have to decrease 15% by 1995. It is believed this drawback could be largely circumvented by mixing the tertiary ethers with tertiary alcohols. Tertiary butyl alcohol (tBA) has a very low atmospheric reactivity and low aldehyde emissions, since no hydrogens are contained in the carbon link to the oxygen. Basis experience acquired with tBA during the 1970s, a gasoline blended with a mixture of ethers and tBA and/or tertiary amyl alcohol should be shippable, Ibid.

The use of zeolites for certain organic transformation reactions is known in the art. Beta-zeolite was first synthesized at Mobil R and D labs and exhibited improved thermal and acid stability over previously synthesized zeolites.

One of the earliest disclosures of β-zeolite was in U.S. Pat. No. 3,308,069 (1967) to Wadinger et al.

J. B. Higgins, et al. of Mobil Research and Development published an article in *Zeolites*, 1988, Vol. 8, November, 446–452 titled "The Framework Topology of Zeolite Beta." In the article Higgins et al. disclose what is known about the framework topology of β-zeolite. The information has been determined using a combination of model building, distance-least-square refinement and powder pattern simulation.

In an article titled "Cumene Disproportionation over Zeolite Beta I. Comparison of Catalytic Performances and Reaction Mechanisms of Zeolites," Applied Catalysis, 77 (1991) 199–207, Tseng-Chang Tsai, Chin-Lan Ay and Ikai Wang disclose a study demonstrating that cumene disproportionation can be applied as a probe reaction for zeolite structure. It is revealed that β-zeolite would have application potential in the production of diisopropylbenzene for reasons of activity, selectivity and stability.

In a second part of the article by Tsai et al., "II. Stability Enhancement with Silica Deposition and Steam Pretreatment", Ibid, pp. 209–222, Tsai and Wang disclose their development of two methods to improve the stability of β-zeolite, silica deposition and steam pretreatment.

E. Bourgeat-Lami et al. have published an article discussing their study on the effects of calcination of zeolite beta, as synthesized, or after ammonium-exchange. See "Stability of the Tetrahedral Aluminum Sites in Zeolite Beta," E. Bourgeat et al., Catalysis Letters, 1990, 5, 265. These researchers came to the conclusion that the tetrahedral aluminum sites disappearing upon calcination can be readily restored by a simple treatment in ammonium nitrate. The parent sample of β-zeolite with a Si/Al ratio of 16.9 was synthesized at 130° C. using tetraethylammonium hydroxide (TEA) as template. The NMR spectrum indicated a dealumination corresponding to about 25%. When this material was treated with ammonium nitrate solution, washed and over dried at 70° C., the signal of octahedral aluminum was no longer detected while that at 53 ppm narrowed and increased to 95% of its original value.

An article titled "Beta-Zeolite as Catalyst or Catalyst Additive for the Production of Olefins During Cracking or Gas Oil," was written by L. Bonetto et al., 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that β-zeolite could be used alone or combined with Y-zeolite as a suitable zeolite component. Various catalysts were studied with respect to minimization of diffusional requirements and zeolite stability.

Japanese Patent 007432 teaches the use of zeolites to make dialkyl ethers containing primary or secondary alkyl groups.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

U.S. Pat. No. 4,419,220, to Mobil, discloses a process for dewaxing a hydrocarbon feedstock containing straight chain paraffins which comprises contacting the feedstock with a β-zeolite catalyst having a Si:Al ratio of at least 30:1 and a hydrogenation component under isomerization conditions.

Another European Application to Mobil, EPO 0 094 82, discloses simultaneous catalytic hydrocracking and hydrodewaxing of hydrocarbon oils with β-zeolite.

In European Patent Application 0 095 303, to Mobil, there is a disclosure of dewaxing distillate fuel oils by the use of β-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising β-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

U.S. patent application Ser. No. 08/096,873 concerns an improved process for preparing methyl tertiary butyl ether (MTBE) along with isobutylene and, optionally diisobutylene in one step by the reaction of tertiary butanol and methanol in the presence of a catalyst comprising β-zeolite or β-zeolite modified with a metal selected from the group consisting of Groups VB, VIIB, and VIII of the Periodic Table.

U.S. patent application Ser. No. 08/057,373 concerns an improved process for preparing ethyl tertiary butyl ether (ETBE) in one step by reaction of tertiary butanol and ethanol in the presence of β-zeolite modified with Groups IB, VB, VIB, VIIB and VIII.

U.S. patent application No. 08/148,248 concerns the use of a palladium/platinum modified β-zeolite for the one-step synthesis of methyl tertiary butyl ether (MTBE).

A number of U.S. patents, and allowed U.S. applications, and applications assigned to Texaco Chemical Co. disclose methods of making alkyl tertiary alkyl ethers, including MTBE and ETBE, in one step, from tert-butanol rather than isobutylene.

These include: U.S. Pat. Nos. 4,822,921, 4,827,048, 5,099,072, 5,081,318, 5,059,725, 5,157,162, 5,162,592, 5,157,161, 5,183,947 and allowed U.S. application Ser. Nos. 07/917,218, 07/878,121, 07/917,885.

Some of the limitations present in the MTBE catalyst systems generally available in the art include loss of activity at temperatures above 120° C., deactivation due to the presence of peroxides and other organic components in the feedstock, lower than desirable selectivity and the requirement of multiple steps to accomplish the synthesis and separation of the product.

From the art available which is related to the synthesis of alkyl tertiary alkyl ethers it is apparent methods have become available in the recent past for one step synthesis from alcohols and butanol using various catalysts. However there is still a need for identifying catalysts which demonstrate improved catalyst life without sacrificing long-term productivity and good conversion levels.

It would represent a significant advance in the art if tertiary butanol, instead of isobutylene and methanol could be reacted to form MTBE in one-step over a modified β-zeolite catalyst which exhibits high levels of productivity and conversion for over 2000 hours of service.

SUMMARY OF THE INVENTION

In accordance with certain of its aspects, the novel method of this invention comprises preparing alkyl tertiary alkyl ethers, particularly methyl tertiary butyl ether (MTBE), from tertiary butyl alcohol and methanol in the presence of a catalyst comprising β-zeolite modified with one or more metals from Group IA and IIIB at an elevated temperature and pressure. Examples demonstrate the particular effectiveness of lithium and rare earth metal-modified β-zeolite. The production of substantial amounts of isobutylene is also documented.

In another embodiment the β-zeolite is modified with silicon-containing reagents and phosphorous-containing modifiers.

DESCRIPTION OF THE INVENTION

Figure 1:
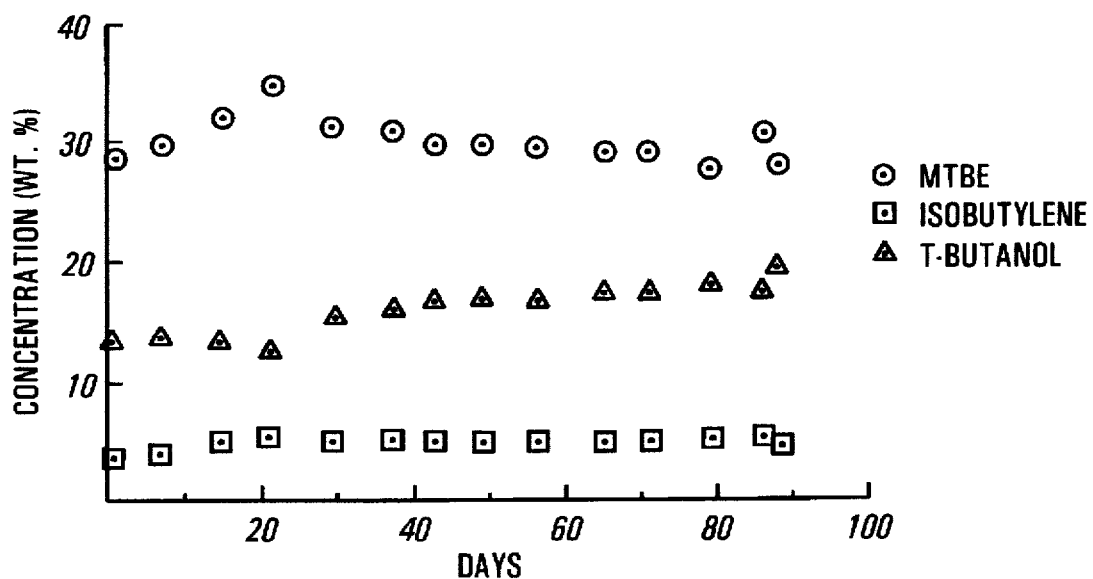
FIG. 1 represents an analysis of levels of concentration of MTBE, isobutylene and t-butanol in the crude product over an 88 day period where catalyst was an unmodified β-zeolite.

Preparation of the product of this invention may be carried out typically by reacting tertiary butyl alcohol and methanol in the presence of other organic oxygenates and in the presence of an etherification catalyst. The etherification is carried out in one-step and the catalyst preferably comprises β-zeolite modified with one or more metals selected from the group consisting of Group IA and IIIB of the Periodic Table.

The reaction can be represented by the following:

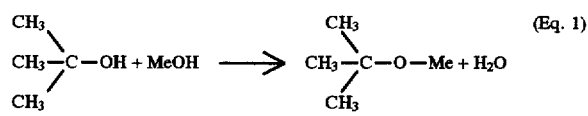

Generally the methanol and t-butanol coreactants may be mixed in any proportion in order to generate the desired methyl t-butyl ether (MTBE) and isobutylene, but preferably the molar ratio of primary alcohol to t-butanol in the feed mixture should be between 10:1 and 1:10, if the yield of desired MTBE is to be maximized. In order to achieve maximum selectivity to MTBE, and optimum conversion per pass, an excess of primary alcohol in the liquid feed is desirable. The most preferred methanol or ethanol-to-tertiary butanol molar ratio is from 1:1 to 5:1.

In certain circumstances, it may be particularly desirable that the tBA conversion be high enough (e.g. 70% or greater), such that the crude product mix phase separates into an isobutylene-MTBE product-rich phase and a heavier aqueous methanol phase. Preferably such a product phase separation would be achieved at as low an etherification temperature as possible, but it is particularly observed in the range 140°–200° C.

The synthesis of Eq. 1 can be conducted where the t-butanol and methanol reactants are mixed with certain other components including water, ketones such as acetone ($Ac_2O$) and methyl ethyl ketone (MEK), peroxides and hydroperoxides such as di-t-butyl peroxide (DTBP) and allyl t-butyl peroxide (ATBP), and t-butyl hydroperoxide (TBHP), as well as esters such as t-butyl formate (TBF). Typically each of said classes of components makes up less than 10% of the total feed mixture.

It has been discovered in the instant invention that ε-zeolite modified with lithium and rare earth lanthanide herein disclosed give conversion levels of ca. 70% for over 2000 hours of service, without a loss of tBA conversion levels and with improved MTBE productivity in comparison with the prior art. This constitutes an important advantage in a commercial setting.

The instant one-step process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. In particular, reaction of ethanol with tertiary butanol would yield ethyl t-butyl ether (ETBE). Alternatively a mixture of alcohols, e.g., a mixture of $C_1$–$C_5$ alcohols, could be reacted to give a mixture of alkyl tert-alkyl ethers.

In the modified catalyst of the instant invention good results were realized using certain crystalline aluminosilicate zeolites as catalysts for the reaction represented in Eq. 1. Particularly effective were the isostructural group of β-zeolites.

β-zeolite was first synthesized at the Mobil Research and Development Laboratories. It exhibited improved thermal and acid stability over previously synthesized zeolites, Higgins et al., supra, p. 446.

The composition of β-zeolite is described in U.S. Pat. Nos. 3,308,069; 4,419,220; 4,518,485 and 4,740,292. In those references, β-zeolite is generally described as follows:

β-zeolite is a crystalline aluminosilicate having a pore size greater than 5 Angstroms. The composition of the zeolite, as described in U.S. Pat. No. 3,308,069, in its as synthesized form may be expressed as follows:

$$[XNa(1.0\pm0.1-X)TEA]AlO_2 \cdot YSiO_2 \cdot WH_2O$$

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, supra, p. 446, the first clues to the crystal structure of β-zeolite were evidenced from chemical and physical property measurements. Ion-exchange isotherms of Na-β at 25° C. indicated that cations as large as tetraethylammonium ($TEA^+$) exchanged completely into the pore system. This behavior suggests that beta contains at least 12-membered rings opening into channels, because $TEA^+$ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 $g/cm^3$ ruled out undimensional pore systems such as those in ZSM-12, ZSM-22, ZSM-23 and ZSM-48. Structural similarities among beta, mordenite and ZSM-12 were suspected because all three may be synthesized in $Na^+$-$TEA^+$ systems from highly siliceous batch compositions. Further, β-zeolite is easily synthesized in the $SiO_2/Al_2O_3$ range of 30–50. This lies between $TEA^+$ mordenite (typically 10–30) and ZSM-12 (typically, >60), suggesting the beta framework contains large fractions of both 4- and 5-membered rings.

In the Tsai and Wang reference, supra, part II, p. 209, stability enhancement is discussed. Two methods, silica deposition and steam pretreatment, have been developed to substantially improve β-zeolite stability.

At comparable conversion levels, the alpha value decreases from 0.23 for unmodified β-zeolite to 0.09 after mild steam pretreatment. Where β-zeolite is steam pretreated, apparently acid strength of the zeolite is enhanced and the yield of aromatics is increased, Ibid, p. 213.

In the fully base-exchanged form, β-zeolite has the composition:

$$[X/n)M(1\pm0.1-X)H]AlO_2 \cdot YSiO_2 \cdot WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Beta-zeolite is characterized by the following X-ray diffraction pattern:

d Values of Reflection in β-zeolite
11.40±0.2
7.40±0.2
6.70±0.2
4.25±0.1
3.97±0.1
3.00±0.1
2.20±0.1

The preferred forms of β-zeolite are the highly acidic, high silica forms, having silica-to-alumina mole ratio of at least 10:1, and preferably in the range of 10:1 to 50:1 in the as-synthesized form. A narrower range of 20:1 to 30:1 is preferred. It has been found, in fact, that β-zeolite may be prepared with silica-to-alumina mole ratios above the 200:1 maximum specified in U.S. Pat. No. 3,308,069 and these forms of the zeolite may perform well in the process. Ratios of 50:1, or even higher, may be used where available.

Particularly effective in the subject synthesis of MTBE are the β-zeolites modified with one or more metals from Group IA and IIIB.

Illustrative of suitable β-zeolites for the practice of this invention include Valfor C806β, Valfor CP815β and Valfor C861. Valfor® is the registered trademark of the PQ Corporation. Valfor® C806β zeolite is β-zeolite powder in template cation form. It is a high silica shape selective zeolite which contains the organic template used in the crystallization step, having been isolated after filtration and washing of the synthesis product. C806β has a $SiO_2/Al_2O_3$ molar ratio of 23–26; the crystal size is 0.1–0.7 um; the surface area after calcination is about 700–750 m²/g; the cyclohexane adsorption capacity after calcination is 19–24 g/100 g; $Na_2O$ content is about 0.5–1.0% by weight anhydrous; and, the organic content is about 11–13% by weight, on a water-free basis.

Valfor® C815β zeolite is a calcined β-zeolite powder in hydrogen, sodium form. It is similar to C806β except the product has been calcined to decompose the organic template. C815β is a high silica, shape selective aluminosilicate with a large pore diameter. C815β also has a $SiO_2/Al_2O$ molar ratio of about 23–26; the crystal size, surface area, cyclohexane adsorption capacity and $Na_2O$ are all within the same ranges as given for C806β. Said beta-zeolites may be formed with a Group III or Group IV oxide binder, such as alumina or silica. The beta-zeolite content of the formed catalyst may be 5% to 95%, but preferably the beta content is 30% to 80%.

Valfor® C861β is an extrudate made of 80% C815β powder and 20% alumina powder.

The metals useful for modifying the zeolite in the instant invention comprise those from Group IA and IIIB of the Periodic Table.

Group IA includes the alkali metals from the group consisting of lithium, sodium, potassium, rubidium and cesium. Zeolites modified with each of these alkali metals, as well as combinations thereof, exhibit the improved catalyst life. The preferred alkali metal is lithium.

Members of Group IIIB metals which are useful for modifying zeolites in the instant invention include each of the lanthanide elements, as well as lanthanum, scandium plus yttrium. Suitable lanthanides include cerium, praseodymium, terbium, neodymium, dysprosium, europium, samarium, ytterbium, thulium, promethium, gadolinium, holmium, erbium, and lutetium, as well as mixtures thereof, plus lanthanum itself. The preferred Group IIIB metals are the mixed rare earth metals (the lanthanides plus lanthanum), and lanthanum alone.

Said beta-zeolites are preferably impregnated with said specified metals as their salts, particularly their metal nitrate or chloride salts, in an aqueous, alcoholic, or ketonic media over a period of 1–24 hours, then the solids are filtered off and treated with 1 liter of 0.2M rare earth chloride solution. The mix is a again slurried at 40°–100° C. for 1 to 24 hours. The exchanged zeolite was then recovered by filtration, washed with distilled water about 20 times, dried at an elevated temperature (e.g. 120° C.) overnight and calcined at 300°–800° C. (e.g. 540° C.) for 1 to 24 hours. Optionally said impregnated β-zeolite may be steamed in the temperature range 300° to 800° C., and/or reduced in a stream of hydrogen at 100° to 500° C.

Example 1 demonstrates the preparation of the lithium, rare earth-exchanged β-zeolite catalysts. Salts of lithium, and lanthanum such as their chloride salts, in anhydrous or hydrated forms were dissolved in water, alcohol, or acetone and the β-zeolites were added, in most cases, in the form of extrudates. The catalysts were then calcined by heating to 300° to 800° C., optionally steamed in the temperature range 300° to 800° C., and/or optionally reduced in a stream of hydrogen at 200° C.

In a second embodiment, demonstrated in Examples 3–6, the zeolite is modified with silicon, phosphorous or halogen-containing reagents. Examples of suitable reagents, include phosphorous pentaoxide, hexamethyldisiloxane and trimethylsilyl chloride.

The amount of the various metals deposited on the zeolite can vary. The amount of each individual metal, lithium or lanthanum can vary from 0.01 to 10.0%. Where lithium and lanthanum are deposited on C861β the preferred weight percent is from 0.1% to 5.0%.

Said catalysts may be in the form of powders, pellets, granules, spheres, shapes and extrudates. The examples described herein demonstrate some advantages in the use of extrudates.

The reaction may be carried out in either a stirred slurry reactor or in a fixed bed continuous flow reactor. The catalyst concentration should be sufficient to provide the desired catalytic effect. Said catalysts may be formed in the presence of a binder, such as Group III or Group IV oxide, including alumina or silica. Said binders may comprise 5% to 95% of the formed catalyst.

Etherification can generally be conducted at temperatures from 20° to 250° C. the preferred range is 80° to 200° C. Good results are observed throughout this temperature range. The total operating pressure may be from 0 to 1000 psig, or higher. The preferred pressure range is 50 to 500 psig.

Typically, MTBE is generated continuously in up to ca. 40 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated in the following examples using the equation:

$$\frac{(\text{Mole \% of } tBA \text{ in Feed} - \text{Mole \% of } tBA \text{ in Product})}{\text{Mole \% of } tBA \text{ in Feed}} \times 100$$

Figure 2:
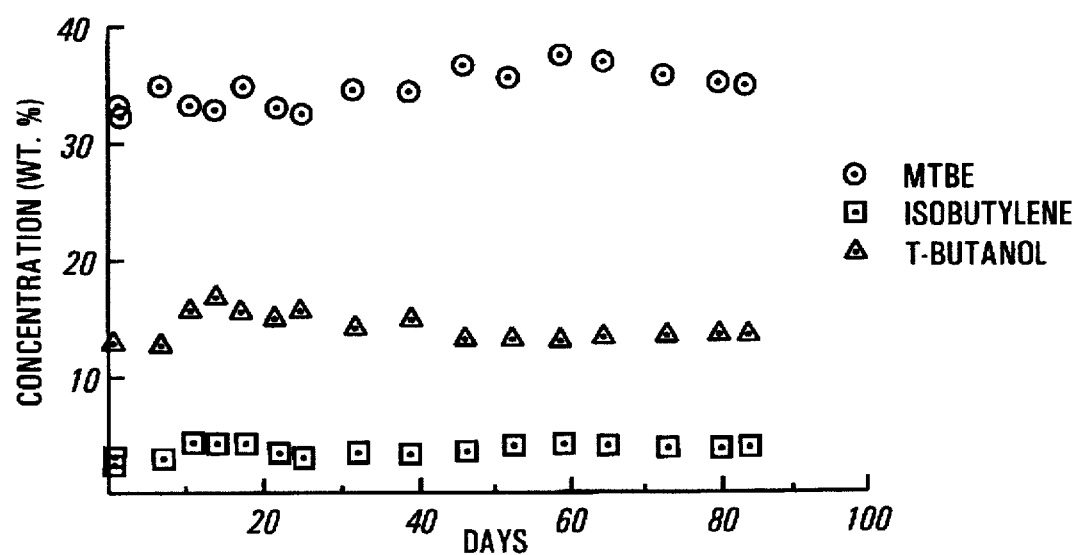
FIG. 2 plots the concentrations of the same products in the crude product over a period of 80 plus days using the lithium, rare earth-modified β-zeolite catalyst of this invention.

The accompanying examples illustrate:

a) The production of MTBE/isobutylene from crude t-butanol/methanol using a β-zeolite catalyst over an extended period, where tBA conversion levels drop from 71% to 62%–63% over the 80+ day run (see Comparative Example A, Table 1) and the tBA concentration in the effluent rises from 13% to ca. 19% (see FIG. 1).

b) The production of MTBE/isobutylene from crude tBA/ MeOH using a lithium, rare earth-modified β-zeolite catalyst where over an extended period (80+ days), the t-butanol conversion remained ca. 70% (See Example 2 and Table 2), while the tBA effluent concentration holds steady at ca. 13% (see FIG. 2).

c) The production of MTBE/isobutylene from t-butanol/ methanol feedstock using a series of β-zeolite catalysts where the zeolite is modified with phosphorous pentaoxide (Table 3), hexamethyldisiloxane (Table 4) and trimethylsilyl chloride (Tables 5 and 6). Product phase separation is realized in these examples at higher operating temperatures (140° C.–180° C.).

COMPARATIVE EXAMPLE A

This example illustrates the production of methyl t-butyl ether from crude t-butanol/methanol feedstock using a B-zeolite catalyst.

Synthesis was conducted in a tubular reactor (½" i.d., 12" long) constructed of 316 stainless steel, operated upflow, and mounted in a furnace, controllable to ±1.0° C. and fitted with pumps allowing flow control to ±1 cc/hr. The reactor was also fitted with a pressure regulating device and equipment for monitoring temperature, pressure and flow rate.

The reactor was charged at the beginning of the experiment with 25 cc of β-zeolite (CP861-DL from PQ Corp., ¹⁄₁₆, diameter extrudates). A screen of glass wool was placed at the top and bottom of the reactor to ensure the catalyst would remain in the middle portion.

The catalyst bed was treated with crude t-butanol/ methanol (1:2 molar mix) also containing significant quantities of water, acetone ($Ac_2O$), isopropanol (2-PrOH), methyl ethyl ketone (MEK), t-butyl formate (TBF) and di-t-butyl peroxide (DTBP). This mix was fed upflow at a rate of 50 cc/hr, while the reactor was held at 120° C., using a total pressure of 300 psi. Samples of crude product effluent were collected periodically on stream, in 3.6 ss bombs, and analyzed by glc.

Typical analyses data for samples taken over the 88 day duration of this run are summarized in Table 1. Concentrations of MTBE, isobutylene, and t-butanol in this crude product effluents are also plotted in FIG. 1. Typical tBA conversion and MTBE selectivity data are summarized below:

| Sample | Time on Stream(Hrs) | Operating Temp(°C.) | tBA Conv(%) | Molar Selec(%) MTBE | $C_4H_8$ |
|---|---|---|---|---|---|
| 1 | 24 | 120 | 71 | 67 | 14 |
| 4 | 504 | 120 | 73 | 80 | 19 |
| 10 | 1560 | 120 | 62 | 79 | 20 |
| 13 | 2064 | 120 | 63 | 84 | 23 |

TABLE 1

LIFE STUDY - ZEOLITE BETA

| Ex. | Catalyst | MeOH/tBA Molar Ratio | Temp. (°C.) | Time on Stream (Days) | Sample | $H_2O$ | MeOH | $C_4H_8$ | $Ac_2O$ | 2-PrOH | tBA | MEK + MTBE | DME | TBF | $C_8H_{16}$ | DTBP |
|---|---|---|---|---|---|---|---|---|---|---|---|---|---|---|---|---|
| A | C861β | 2:1 | | | FS-1 | 5.9 | 38.8 | — | 0.6 | 6.3 | 46.2 | 2.1 | — | 0.19 | — | — |
| | | | 120 | 1 | →1 | 15.9 | 31.6 | 3.5 | 0.7 | 6.8 | 13.2 | 28.3 | 0.11 | — | 45 | — |
| | | | | 7 | 2 | 15.0 | 30.5 | 3.6 | 0.7 | 6.6 | 13.8 | 29.7 | 0.07 | 0.01 | 3.2 | — |
| | | | | — | FS-2 | 5.6 | 39.2 | — | — | 6.3 | 46.2 | 1.9 | — | 0.19 | — | — |
| | | | | 15 | 3 | 13.5 | 28.9 | 4.3 | 0.7 | 6.2 | 13.6 | 32.0 | 0.04 | 0.01 | 1.6 | — |
| | | | | — | FS-3 | 5.8 | 39.0 | — | 0.6 | 6.3 | 46.4 | 1.7 | — | 0.17 | 0.1 | 0.02 |
| | | | | 21 | →4 | 12.9 | 27.7 | 4.9 | 0.6 | 5.9 | 12.3 | 34.3 | 0.02 | — | 1.0 | — |
| | | | | — | FS-4 | 5.8 | 39.2 | — | 0.6 | 6.3 | 45.8 | 1.9 | — | 0.16 | 0.1 | 0.02 |
| | | | | 29 | 5 | 13.3 | 29.0 | 4.3 | 0.7 | 6.1 | 15.3 | 31.3 | 0.02 | — | 0.6 | — |
| | | | | 37 | 6 | 13.1 | 29.2 | 4.3 | 0.7 | 6.1 | 16.0 | 30.5 | 0.01 | 0.01 | 0.4 | — |
| | | | | 43 | 7 | 12.9 | 30.0 | 4.2 | 0.5 | 6.3 | 16.3 | 29.7 | 0.02 | — | 0.4 | — |
| | | | | — | FS-5 | 5.9 | 39.5 | — | 0.5 | 6.4 | 45.7 | 1.7 | 0.01 | 0.12 | 0.1 | 0.1 |
| | | | | 49 | 8 | 12.8 | 30.0 | 4.2 | 0.5 | 6.3 | 16.5 | 29.5 | 0.02 | — | 0.3 | — |
| | | | | — | FS-6 | 5.8 | 39.5 | — | 0.5 | 6.5 | 45.6 | 1.8 | — | 0.12 | 0.1 | 0.01 |
| | | | | 56 | 9 | 13.0 | 30.1 | 4.3 | 0.5 | 6.4 | 16.4 | 29.2 | 0.02 | — | 0.3 | — |
| | | | | 65 | →10 | 12.7 | 30.5 | 4.2 | 0.5 | 6.4 | 17.3 | 28.3 | 0.02 | — | 0.2 | 0.01 |
| | | | | 71 | 11 | 12.7 | 30.3 | 4.2 | 0.5 | 6.4 | 17.3 | 28.4 | 0.02 | — | 0.2 | — |
| | | | | — | FS-7 | 5.9 | 39.6 | — | 0.4 | 6.5 | 45.5 | 1.7 | — | 0.10 | 0.1 | 0.01 |
| | | | | 79 | 12 | 12.5 | 30.8 | 4.3 | 0.5 | 6.4 | 17.9 | 27.6 | 0.02 | — | 0.2 | — |
| | | | | — | FS-8 | 6.0 | 39.3 | — | 0.5 | 6.6 | 45.6 | 1.7 | — | 0.10 | 0.1 | 0.01 |
| | | | | 86 | →13 | 11.0 | 30.5 | 4.9 | 0.6 | 5.8 | 16.9 | 30.3 | 0.02 | — | 0.02 | — |
| | | | | 88 | 14 | 11.8 | 29.7 | 4.0 | 0.6 | 6.4 | 19.4 | 27.7 | 0.02 | — | 0.02 | — |

EXAMPLE 1

This example illustrates the preparation of lithium, rare earth-exchanged β-zeolite.

To 100 g of β-zeolite (CP861-DL Beta, 80% β-zeolite, 20% alumina binder, from PQ corporation, as ¹⁄₁₆" diameter extrudates) was added 1 liter of 1M lithium chloride solution and the mix slurried at 60° C. for 5 hours). Solids were filtered off and treated with 1 liter of 0.2M rare earth chloride solution. Again the mix was slurried at 60° C. for 5 hours. The exchanged zeolite was then recovered by filtration, washed with distilled water (100 cc) about 20 times, dried at 120° C. overnight, and calcined at 540° C. for 5 hours.

EXAMPLE 2

This example illustrates the production of methyl t-butyl ether from crude t-butanol/methanol feedstock using a lithium, rare earth-treated β-zeolite catalyst.

Following the procedures of comparative Example A, the lithium, rare earth-modified β-zeolite of Example 1 was treated with the same crude 2:1 molar mix of methanol/t-butanol of comparative Example A. Etherification was conducted at 120° C., 300 psi, using a LHSV of 2, for a period of 84 days. Concentrations of each component was followed by glc analyses of the product effluents.

Typical data are given in Table 2 for Samples 1–17, taken over the 84 day duration of this run. Concentrations of MTBE, isobutylene, and t-butanol in the crude product effluents are also plotted in FIG. 2. Typical tBA conversion and MTBE selectivity data are summarized below:

| Sample | Time on Stream(Hrs) | Operating Temp(°C.) | tBA Conv(%) | Molar Selectivity MTBE | $C_4H_8$ |
|---|---|---|---|---|---|
| 1 | 24 | 120 | 72 | 83 | 12 |
| 5 | 336 | 120 | 68 | 82 | 16 |
| 11 | 1104 | 120 | 73 | 89 | 15 |
| 15 | 1752 | 120 | 72 | 87 | 15 |
| 17 | 2016 | 120 | 71 | 86 | 15 |

EXAMPLES 3–6

These examples illustrate the production of methyl t-butyl ether from t-butanol/methanol feedstocks using a series of β-zeolite catalysts modified with silicon, phosphorous and halogen-containing reagents.

Following the procedures of Example 2, a series of modified β-zeolite catalysts were tested for etherification activity using a 1.1:1 methanol/t-butanol feed mix over a range of operating temperatures (120°–180° C.). Concentrations of the t-butanol, methanol, isobutylene and MTBE in the crude effluent products were followed by glc analyses.

Typical data are given in Tables 3–6 for:

a) Beta-zeolite, treated with phosphorous pentaoxide (Table 3).

b) Beta-zeolite, treated with hexamethyldisiloxane (HMDS, Table 4).

c) Two β-zeolite samples, with different alumina binder levels, treated with trimethylsilyl chloride (TSMCl, Tables 5 and 6).

TABLE 2

LIFE STUDY - Li, La-MODIFIED ZEOLITE BETA

| Ex. | Catalyst | MeOH/tBA Molar Ratio | Temp. (°C.) | Time on Stream (Days) | Sample | $H_2O$ | MeOH | $C_4H_8$ | $Ac_2O$ | 2-PrOH | tBA | METHOD 26 MEK + MTBE | DME | TBF | METHOD 27 $C_8H_{16}$ | DTBP |
|---|---|---|---|---|---|---|---|---|---|---|---|---|---|---|---|---|
| 2 | 1 | 2:1 | | | FS-1 | 6.0 | 39.9 | — | — | 6.4 | 45.6 | — | — | — | — | — |
| | | | 120 | 1 | →1 | 12.6 | 29.4 | 3.0 | — | 6.3 | 12.9 | 32.2 | 0.03 | — | 2.1 | — |
| | | | | 1 | 2 | 12.6 | 29.5 | 3.4 | — | 6.2 | 12.6 | 33.1 | 0.03 | — | 2.1 | — |
| | | | | 7 | 3 | 12.5 | 29.3 | 3.4 | — | 6.0 | 12.2 | 34.8 | 0.03 | — | 1.5 | — |
| | | | | — | FS-2 | 6.9 | 33.4 | — | 7.6 | 50.1 | — | — | — | — | — | — |
| | | | | 11 | 4 | 13.6 | 23.1 | 4.2 | — | 6.9 | 15.7 | 33.3 | 0.02 | — | 2.2 | — |
| | | | | 14 | →5 | 13.7 | 23.1 | 4.1 | — | 7.0 | 16.2 | 32.8 | 0.02 | — | 2.1 | — |
| | | | | 18 | 6 | 13.5 | 22.9 | 4.2 | — | 6.7 | 15.5 | 34.4 | 0.02 | — | — | — |
| | | | | 22 | 7 | 13.3 | 25.6 | 3.8 | — | 6.7 | 14.8 | 33.2 | 0.02 | — | 1.3 | — |
| | | | | — | FS-3 | 6.7 | 36.0 | — | — | 7.1 | 48.3 | — | — | — | — | — |
| | | | | 25 | 8 | 14.4 | 25.3 | 3.7 | — | 6.5 | 15.6 | 33.2 | 0.02 | — | 1.5 | — |
| | | | | 32 | 9 | 13.2 | 25.7 | 3.9 | — | 6.3 | 14.0 | 34.4 | 0.02 | — | 1.4 | — |
| | | | | — | FS-4 | 6.6 | 36.6 | — | — | 6.7 | 47.9 | — | — | — | — | — |
| | | | | 39 | 10 | 13.2 | 25.9 | 3.9 | — | 6.4 | 14.2 | 34.1 | 0.01 | — | 1.2 | — |
| | | | | — | FS-5 | 5.8 | 38.6 | — | — | 6.4 | 47.4 | — | — | — | — | — |
| | | | | 46 | →11 | 12.5 | 27.2 | 3.9 | — | 5.7 | 12.9 | 36.6 | 0.01 | — | 0.9 | — |
| | | | | 52 | 12 | 12.3 | 27.1 | 4.0 | — | 5.7 | 12.7 | 35.8 | 0.01 | — | 1.2 | — |
| | | | | 59 | 13 | 12.2 | 26.9 | 4.0 | — | 5.5 | 12.6 | 37.6 | 0.01 | — | 0.9 | — |
| | | | | — | FS-6 | 5.9 | 38.5 | — | — | 6.4 | 47.4 | — | — | — | — | — |
| | | | | 65 | 14 | 12.2 | 27.3 | 4.0 | — | 5.7 | 12.9 | 36.7 | 0.01 | — | 0.9 | — |
| | | | | — | FS-7 | 5.8 | 38.6 | — | — | 6.2 | 47.4 | — | — | — | — | — |
| | | | | 73 | →15 | 12.2 | 27.5 | 3.9 | — | 5.8 | 13.2 | 35.6 | 0.01 | — | 0.7 | — |
| | | | | — | FS-8 | 5.9 | 38.5 | — | — | 6.4 | 47.4 | — | — | — | — | — |
| | | | | 80 | 16 | 12.4 | 27.7 | 3.8 | — | 6.0 | 13.6 | 34.6 | 0.01 | — | 0.8 | — |
| | | | | 84 | →17 | 12.7 | 27.5 | 3.8 | — | 6.0 | 13.6 | 34.5 | 0.01 | — | 0.8 | — |

TABLE 3

| Ex. | Catalyst | MeOH/tBA Molar Ratio | Feed Rate (cc/hr) | Temp. (°C.) | Time On Stream (Days) | SAMPLE | PRODUCT COMPOSITION (Wt %) METHOD 26 | | | | | METHOD 27 | |
|---|---|---|---|---|---|---|---|---|---|---|---|---|---|
| | | | | | | | $H_2O$ | MeOH | $C_4H_8$ | tBA | MTBE | $C_8H_{16}$ | DME |
| 3 | 052-93-6895-117[a] | 1.1:1 | 50 | | | FS-1 | | 31.4 | | 68.2 | | | |
| | | | | 120 | 1 | 1 | 10.1 | 17.4 | 6.9 | 20.1 | 43.5 | 2.9 | 0.02 |
| | | | | | | 2 | 9.8 | 17.5 | 6.9 | 20.3 | 43.2 | 3.3 | 0.02 |
| | | | | 140 | 2 | 3 | 11.7 | 21.2 | 8.5 | 15.6 | 34.3 | 12.6 | 0.13 |
| | | | | | | 4 | 11.6 | 21.4 | 8.5 | 15.7 | 33.9 | 12.9 | 0.13 |
| | | | | 160 | 3 | 5 | 1.4 | 8.0 | 15.5 | 6.6 | 31.5 | 28.4 | 0.46 |
| | | | | | | | 24.7 | 43.8 | 1.4 | 13.7 | 14.0 | 3.3 | 0.26 |
| | | | | | | 6 | 1.6 | 8.6 | 15.3 | 7.3 | 31.8 | 35.0 | 0.46 |
| | | | | | | | 23.9 | 42.8 | 1.9 | 13.0 | 16.0 | 3.6 | 0.26 |
| | | | | | 4 | 7 | 1.1 | 6.8 | 60.1 | 3.0 | 18.7 | 15.6 | 0.31 |
| | | | | | | | 30.4 | 52.4 | 3.5 | 6.7 | 6.3 | 0.5 | 0.20 |
| | | | | | | 8 | 1.4 | 7.5 | 59.0 | 4.1 | 18.8 | 13.0 | 0.27 |
| | | | | | | | 29.7 | 51.2 | 3.9 | 6.5 | 7.0 | 0.4 | 0.18 |

[a]30% Beta-Zeolite/70% alumina, Treated with $P_2O_5$, 4% P, 1/16"E

TABLE 4

| Ex. | Catalyst | MeOH/tBA Molar Ratio | Feed Rate (cc/hr) | Temp. (°C.) | Time On Stream (Days) | SAMPLE | PRODUCT COMPOSITION (Wt %) METHOD 26 | | | | | METHOD 27 | |
|---|---|---|---|---|---|---|---|---|---|---|---|---|---|
| | | | | | | | $H_2O$ | MeOH | $C_4H_8$ | tBA | MTBE | $C_8H_{16}$ | DME |
| 4 | 052-93-2122-000[a] | 1.1:1 | 50 | | | FS-1 | | 31.4 | | 68.2 | | | |
| | | | | 120 | 1 | 1 | 10.6 | 18.2 | 6.3 | 18.6 | 42.2 | 6.1 | 0.04 |
| | | | | | | 2 | 10.6 | 18.1 | 6.3 | 18.5 | 43.2 | 5.2 | 0.04 |
| | | | | 140 | 2 | 3 | 2.6 | 10.3 | 10.9 | 8.3 | 38.5 | 29.2 | 0.3 |
| | | | | | | | 25.1 | 40.0 | 2.0 | 13.2 | 17.2 | 3.9 | 0.2 |
| | | | | | | 4 | 2.4 | 9.9 | 10.8 | 8.0 | 38.3 | 30.3 | 0.3 |
| | | | | | | | 24.8 | 40.7 | 1.8 | 13.2 | 17.0 | 3.8 | 0.2 |
| | | | | | 3 | 5 | 1.8 | 5.6 | 13.3 | 5.7 | 23.4 | 26.4 | 1.4 |
| | | | | | | | 27.6 | 58.9 | 0.9 | 1.8 | 6.1 | 0.7 | 1.4 |
| | | | | | | 6 | 1.4 | 5.2 | 12.3 | 1.8 | 25.3 | 27.9 | 1.4 |
| | | | | | | | 27.9 | 57.8 | 0.8 | 5.3 | 6.5 | 0.9 | 1.4 |

[a]80% Beta-Zeolite/20% Alumina, Treated with HMDS

TABLE 5

| Ex. | Catalyst | MeOK/tBA Molar Ratio | Feed Rate (cc/hr) | Temp. (°C.) | Time On Stream (Days) | SAMPLE | PRODUCT COMPOSITION (Wt %) METHOD 26 | | | | | METHOD 27 | |
|---|---|---|---|---|---|---|---|---|---|---|---|---|---|
| | | | | | | | $H_2O$ | MeOH | $C_4H_8$ | tBA | MTBE | $C_8H_{16}$ | DME |
| 5 | 052-93-2122-000[a] | 1.1:1 | 50 | | | FS-1 | | 31.4 | | 68.2 | | | |
| | | | | 120 | 1 | 1 | 9.6 | 17.6 | 6.5 | 19.9 | 43.8 | 3.4 | 0.03 |
| | | | | | | 2 | 9.8 | 17.8 | 6.0 | 20.1 | 43.3 | 3.1 | 0.02 |
| | | | | 140 | 2 | 3 | 10.4 | 20.5 | 8.3 | 13.9 | 36.0 | 14.2 | 0.15 |
| | | | | | | 4 | b | | | | | | |
| | | | | | | | 19.9 | 33.8 | 3.7 | 14.3 | 24.5 | 5.2 | 0.19 |
| | | | | | 3 | 5 | 0.2 | 4.4 | 13.8 | 4.9 | 30.5 | 25.1 | 1.2 |
| | | | | | | | 29.2 | 53.5 | 0.9 | 6.6 | 8.7 | 1.0 | 1.1 |

TABLE 5-continued

| Ex. | Catalyst | MeOK/tBA Molar Ratio | Feed Rate (cc/hr) | Temp. (°C.) | Time On Stream (Days) | SAMPLE | H₂O | MeOH | C₄H₈ | tBA | MTBE | C₈H₁₆ | DME |
|---|---|---|---|---|---|---|---|---|---|---|---|---|---|
| | | | | | | 6 | 0.6 | 6.7 | 13.2 | 2.8 | 28.6 | 28.0 | 1.1 |
| | | | | | | | 28.7 | 53.1 | 0.8 | 7.5 | 8.5 | 1.2 | 1.0 |

ᵃ80% Beta-Zeolite/20% Alumina, Treated with TMSCl
bInsufficient Sample for Analysis

TABLE 6

| Ex. | Catalyst | MeOK/tBA Molar Ratio | Feed Rate (cc/hr) | Temp. (°C.) | Time On Stream (Days) | SAMPLE | H₂O | MeOH | C₄H₈ | tBA | MTBE | C₈H₁₆ | DME |
|---|---|---|---|---|---|---|---|---|---|---|---|---|---|
| 6 | 052-93-2112-000ᵃ | 1.1:1 | 50 | | | FS-1 | 0.1 | 31.1 | | 68.4 | | | |
| | | | | 120 | 1 | 1 | 10.0 | 17.3 | 8.1 | 20.8 | 42.2 | 1.8 | 0.01 |
| | | | | | | 2 | 10.0 | 17.3 | 8.1 | 20.8 | 42.3 | 1.8 | 0.01 |
| | | | | 140 | 2 | 3 | 11.2 | 20.0 | 9.5 | 15.4 | 36.5 | 10.0 | 0.08 |
| | | | | | | 4 | 11.1 | 19.1 | 10.3 | 15.3 | 36.7 | 10.0 | 0.08 |
| | | | | 160 | 3 | 5 | 1.6 | 8.4 | 20.0 | 6.0 | 30.2 | 33.9 | 0.33 |
| | | | | | | | 25.9 | 42.3 | 2.2 | 11.1 | 15.1 | 3.0 | 0.18 |
| | | | | | | 6 | 2.0 | 9.4 | 22.1 | 7.0 | 31.4 | 33.5 | 0.31 |
| | | | | | | | 26.1 | 41.7 | 3.1 | 12.7 | 14.3 | 2.2 | 0.17 |
| | | | | 180 | 4 | 7 | 1.0 | 6.6 | 61.3 | 3.2 | 18.0 | 14.1 | 0.17 |
| | | | | | | | 30.9 | 51.3 | 3.5 | 6.9 | 6.6 | 0.4 | 0.07 |
| | | | | | | 8 | 0.8 | 6.3 | 61.8 | 2.9 | 17.7 | 14.0 | 0.19 |
| | | | | | | | 30.9 | 52.2 | 3.5 | 6.3 | 6.4 | 0.4 | 0.07 |

ᵃ30% Beta-Zeolite/70% alumina, Treated with TSMCl, 1/16"E

What is claimed is:

1. A catalyst composition comprising a β-zeolite modified with one or more metals selected from Group IA and Group IIIB of the Periodic Table wherein the concentration of metal deposited on said β-zeolite may vary from 0.01% to 10.0% for each metal.

2. The catalyst composition of claim 1 wherein the β-zeolite has a silica-to-alumina molar ratio of at least 10:1.

3. The catalyst composition of claim 2 wherein the β-zeolite has a silica-to-alumina mole ratio of 20 to 30.

4. The catalyst composition of claim 3 wherein the β-zeolite is characterized by the following X-ray diffraction pattern:

d Values of Reflection in β-zeolite:
11.40±0.2
7.40±0.2
6.70±0.2
4.25±0.1
3.97±0.1
3.00±0.1
2.20±0.1

5. The catalyst composition of claim 1, further characterized in that the β-zeolite is bound to an oxide binder selected from Group III or IV of the Periodic Table.

6. The catalyst composition of claim 5 wherein the oxide binder comprises 5% to 95% of the formed catalyst.

7. The catalyst composition of claim 5 wherein the Group III oxide is alumina.

8. The catalyst composition of claim 1, wherein the Group IA metal is selected from the group consisting of lithium, sodium, potassium, rubidium and cesium.

9. The catalyst composition of claim 1, wherein the Group IA metal is lithium.

10. The catalyst composition of claim 1, wherein the Group IIIB metal is selected from the group consisting of scandium, yttrium, lanthanum, and the lanthanide elements, as well as mixtures thereof.

11. The catalyst composition of claim 10 wherein the Group IIIB metal is a mixture of lanthanum plus lanthamide elements, known as rare earth metals.

12. The catalyst composition of claim 1 wherein the β-zeolite is modified with lithium and rare earth metals.

13. The catalyst composition of claim 1 wherein the concentrations of metals deposited on said β-zeolite may vary from 0.1 wt % to 5.0 wt %.

* * * * *